United States Patent
Kataoka et al.

(10) Patent No.: US 12,408,815 B2
(45) Date of Patent: Sep. 9, 2025

(54) TOMOGRAPHIC IMAGE PROCESSING DEVICE, TOMOGRAPHIC IMAGE PROCESSING METHOD, PROGRAM, INFORMATION RECORDING MEDIUM, AND PUNCTURE MEMBER

(71) Applicant: RIKEN, Saitama (JP)

(72) Inventors: Yosky Kataoka, Saitama (JP); Sally Danno, Saitama (JP); Toshiyuki Goto, Saitama (JP); Kazuo Funabiki, Saitama (JP); Ichiro Nakahara, Saitama (JP); Akira Mizoguchi, Saitama (JP)

(73) Assignee: RIKEN, Saitama (JP)

( * ) Notice: Subject to any disclaimer, the term of this patent is extended or adjusted under 35 U.S.C. 154(b) by 135 days.

(21) Appl. No.: 18/553,340

(22) PCT Filed: Mar. 30, 2022

(86) PCT No.: PCT/JP2022/015824
§ 371 (c)(1),
(2) Date: Sep. 29, 2023

(87) PCT Pub. No.: WO2022/210834
PCT Pub. Date: Oct. 6, 2022

(65) Prior Publication Data
US 2024/0206703 A1    Jun. 27, 2024

(30) Foreign Application Priority Data
Mar. 31, 2021  (JP) .................................. 2021-060196

(51) Int. Cl.
*A61B 1/00* (2006.01)
*G01N 21/64* (2006.01)
(Continued)

(52) U.S. Cl.
CPC ... *A61B 1/000095* (2022.02); *G01N 21/6458* (2013.01); *G06T 7/0012* (2013.01); *G06T 11/003* (2013.01)

(58) Field of Classification Search
CPC .............. A61B 1/000095; A61B 1/043; G01N 21/6458; G06T 7/0012; G06T 11/003
See application file for complete search history.

(56) References Cited

U.S. PATENT DOCUMENTS

| | | | |
|---|---|---|---|
| 5,334,150 A | 8/1994 | Kaali | |
| 6,594,518 B1* | 7/2003 | Benaron | A61B 5/1459 600/478 |

(Continued)

FOREIGN PATENT DOCUMENTS

| | | |
|---|---|---|
| EP | 0726784 B1 | 8/1996 |
| EP | 1006875 A1 | 6/2000 |

(Continued)

OTHER PUBLICATIONS

International Search Report dated Jun. 14, 2022 for PCT Appl. No. PCT/JP2022/015824.

(Continued)

*Primary Examiner* — Timothy R Newlin
(74) *Attorney, Agent, or Firm* — Ohlandt, Greeley and Perle, L.L.P.

(57) ABSTRACT

A tomographic image processing device generates a pseudo tomographic image from a moving image in which a cross section is captured via a light-receiving surface of a puncture member that punctures a living body. Herein, an acquirer acquires the moving image in which the cross section is captured via the light-receiving surface of the puncture member that punctures the living body. A corrector performs image correction of each frame of the moving image, based on a shape of the light-receiving surface. A tracker tracks a candidate for a picture of tissue of the living body that (Continued)

satisfies a desired tracking condition. An estimator estimates a representative vector, based on a movement vector of the candidate. An extractor extracts a candidate in which the movement vector is similar to the representative vector. A calculator calculates, based on a drawing position in a frame in which a picture of the extracted candidate is drawn in the moving image and an order of the frame, an arrangement position in which the picture of the candidate needs to be arranged. A generator generates a pseudo tomographic image of the living body by drawing the picture of the extracted candidate in the calculated arrangement position.

19 Claims, 20 Drawing Sheets

(51) Int. Cl.
G06T 7/00 (2017.01)
G06T 11/00 (2006.01)

(56) References Cited

U.S. PATENT DOCUMENTS

| | | | | |
|---|---|---|---|---|
| 9,188,973 | B2* | 11/2015 | Tenney | H04N 7/181 |
| 2007/0161853 | A1 | 7/2007 | Yagi et al. | |
| 2013/0184842 | A1 | 7/2013 | Mora et al. | |
| 2015/0272423 | A1* | 10/2015 | Ito | A61B 1/00055 |
| | | | | 600/476 |
| 2016/0189371 | A1* | 6/2016 | Krishna Rao | G06T 7/0012 |
| | | | | 382/128 |
| 2016/0321821 | A1* | 11/2016 | Brown | G06T 3/20 |
| 2017/0206640 | A1* | 7/2017 | Ichiki | A61B 1/00154 |
| 2018/0353158 | A1* | 12/2018 | Frinking | A61B 8/5246 |
| 2018/0353244 | A1* | 12/2018 | Kashima | A61B 18/00 |
| 2019/0239718 | A1* | 8/2019 | Iwaki | G06T 7/0012 |
| 2020/0084379 | A1* | 3/2020 | Ikeda | A61B 1/00188 |
| 2020/0098104 | A1* | 3/2020 | Kashima | G06T 7/0012 |
| 2020/0286224 | A1* | 9/2020 | Grass | G06T 11/003 |
| 2021/0123999 | A1* | 4/2021 | An | G01R 33/56308 |
| 2021/0225047 | A1* | 7/2021 | Pawar | G01R 33/4818 |
| 2021/0282630 | A1* | 9/2021 | Kikuchi | A61B 1/0655 |
| 2022/0172827 | A1 | 6/2022 | Endo | |
| 2022/0261967 | A1* | 8/2022 | Nakamura | A61B 1/000095 |
| 2022/0296082 | A1* | 9/2022 | Shiraki | A61B 1/00006 |
| 2024/0411675 | A1* | 12/2024 | Abbas | G06F 11/3688 |

FOREIGN PATENT DOCUMENTS

| | | |
|---|---|---|
| JP | 8-503401 A | 4/1996 |
| JP | 2013-505043 A | 2/2013 |
| WO | 2012-124092 A1 | 9/2012 |
| WO | 2021039438 A1 | 3/2021 |

OTHER PUBLICATIONS

Atsushi Seki, Kazuhiro Watanabe, "Fluorescence Measurement by using Needle-Shaped Optical Fiber", The Institute of Electronics, Information and Communication Engineers (IEICE) 2019 General Conference, Optical Fiber Applied Technology (B-13), Date of Issue Mar. 5, 2019.

Extended European Search Report dated Feb. 28, 2025 for European Application No. 22781045.4.

* cited by examiner

Bamboo
θ=60°

Bamboo $\theta = 60°$

TOMOGRAPHIC IMAGE PROCESSING DEVICE, TOMOGRAPHIC IMAGE PROCESSING METHOD, PROGRAM, INFORMATION RECORDING MEDIUM, AND PUNCTURE MEMBER

TECHNICAL FIELD

The present disclosure relates to a tomographic image processing device, a tomographic image processing method, a program, an information recording medium, and a puncture member for generating a pseudo tomographic image of a living body from a moving image in which a cross section of the living body is captured via a light-receiving surface of the puncture member that punctures the living body.

BACKGROUND ART

A technique for observing the inside of a living body by puncturing the living body with a puncture member has been proposed.

For example, Patent Literature 1 discloses a related art in which, in order to inspect a solid organ of a subject, a needle is introduced into a predetermined area of the solid organ, an optical probe is inserted through a lumen of the needle, and the predetermined area is captured by using the optical probe.

In the related art, the optical probe is disposed in the solid organ through the needle, and includes an optical fiber bundle and a ferule for protecting a distal end of the optical fiber bundle.

In the related art, the ferule includes a shank, a head, and a case that covers the optical fiber bundle and the shank.

In the related art, the head of the ferule has a length in which the optical probe can capture the solid organ while the case is held inside the needle.

Meanwhile, Non Patent Literature 1 discloses a technique capable of measuring a fluorescent spectrum by etching, into a needle shape, an end of one optical fiber having a diameter of 125 μm, and measuring strength when excitation light is introduced from the end.

CITATION LIST

Patent Literature

Patent Literature 1: Unexamined Japanese Patent Application Publication (Translation of PCT Application) No. 2013-505043

Non Patent Literature

Non Patent Literature 1: Atsushi SEKI, Kazuhiro WATANABE, Fluorescence Measurement by using Needle-Shaped Optical Fiber, The Institute of Electronics, Information and Communication Engineers (IEICE) 2019 General Conference, Optical Fiber Applied Technology (B-13), Lecture Number B-13-23, https://www.ieice.org/publications/conferences/summary.php?id=CONF0000122214, https://www.ieice-taikai.jp/2019general/jpn/webpro/_html/cs.html, Date of Issue Mar. 5, 2019.

SUMMARY OF INVENTION

Technical Problem

In the related art, a range of a field of view in which capturing is performed is limited to a thickness of an optical fiber bundle.

Thus, in the related art, a scene of a shape and the like of tissue of a living body across a range exceeding the range of the field of view, and a scene of a shape and the like of tissue of a living body in a depth direction cannot be captured.

Therefore, a technique capable of acquiring a tomographic image of tissue of a living body at a resolution at a cell level is strongly desired.

The present disclosure solves the problem described above, and relates to a tomographic image processing device, a tomographic image processing method, a program, an information recording medium, and a puncture member for generating a pseudo tomographic image of a living body from a moving image in which a cross section of the living body is captured via a light-receiving surface of the puncture member that punctures the living body.

Solution to Problem

A tomographic image processing device according to the present disclosure
  acquires a moving image in which a cross section of a living body is captured via a light-receiving surface of a puncture member that punctures the living body,
  performs image correction of each frame of the acquired moving image, based on a shape of the light-receiving surface,
  tracks a candidate for a picture of tissue of the living body that satisfies a desired tracking condition in the moving image on which the image correction is performed,
  estimates, based on a movement vector of the tracked candidate, a representative vector in the moving image on which the image correction is performed,
  extracts a candidate in which the movement vector is similar to the estimated representative vector,
  calculates, based on a drawing position in a frame in which a picture of the extracted candidate is drawn in the moving image and an order of the frame, an arrangement position in which the picture of the extracted candidate needs to be arranged, and
  generates a pseudo tomographic image of the living body by drawing the picture of the extracted candidate in the calculated arrangement position.

A puncture member according to the present disclosure is a thin wire acquired by bundling optical fibers, wherein
  the puncture member punctures a living body in a longitudinal direction of the thin wire, and
  one of stumps of the thin wire is a light-receiving surface for capturing a cross section of the living body.

Advantageous Effects of Invention

The present disclosure can provide a tomographic image processing device, a tomographic image processing method, a program, an information recording medium, and a puncture member for generating a pseudo tomographic image of a living body from a moving image in which a cross section of the living body is captured via a light-receiving surface of the puncture member that punctures the living body.

DESCRIPTION OF EMBODIMENTS

Embodiments according to the present disclosure are described below. Note that the present embodiment is used for description, and does not limit the scope of the present disclosure. Therefore, a person skilled in the art can adopt an embodiment in which each element or all elements of the present embodiment are replaced with equivalent elements. Further, an element described in each example can also be appropriately omitted according to a use. In this way, all embodiments constituted based on the principle of the present disclosure are included in the scope of the present disclosure.

Configuration

Figure 1:
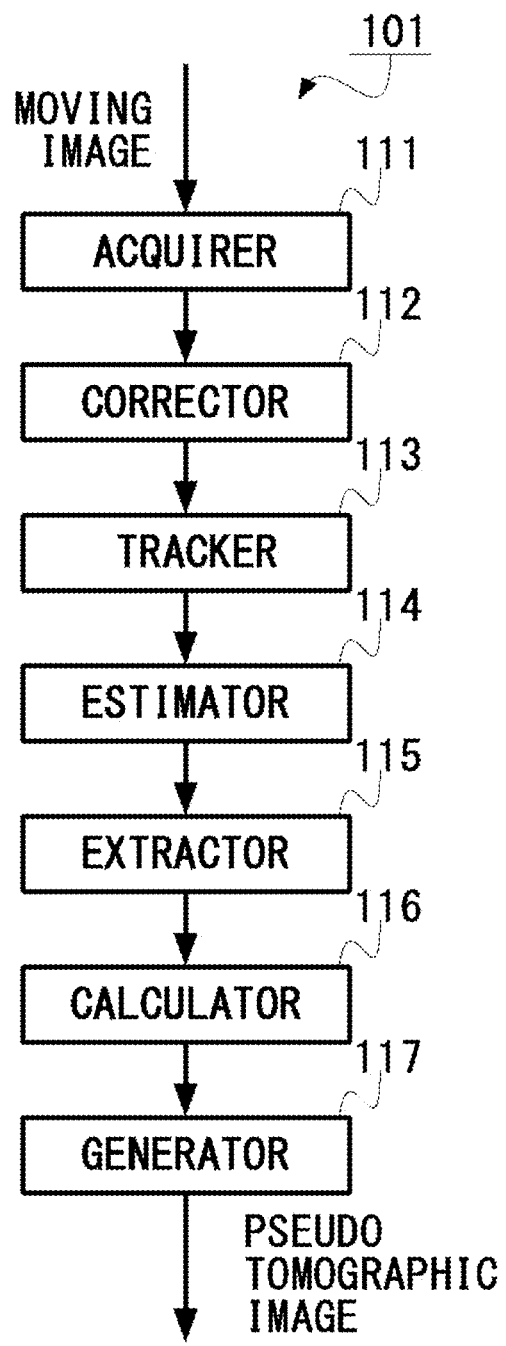
FIG. 1 is an explanatory drawing illustrating an overview configuration of a tomographic image processing device according to an embodiment of the present disclosure.

FIG. 1 is an explanatory drawing illustrating an overview configuration of a tomographic image processing device according to an embodiment of the present disclosure. Hereinafter, the overview is described with reference to FIG. 1.

As illustrated in FIG. 1, a tomographic image processing device 101 according to the present embodiment includes an acquirer 111, a corrector 112, a tracker 113, an estimator 114, an extractor 115, a calculator 116, and a generator 117.

The tomographic image processing device 101 is typically achieved by a program executed by a computer. The computer is connected to various output devices and input devices, and transmits and receives information to and from the devices.

The program executed by the computer can be distributed and sold by a server communicably connected to the computer. In addition, the program can be recorded in a non-transitory information recording medium such as a compact disk read only memory (CD-ROM), a flash memory, and an electrically erasable programmable ROM (EEPROM), and then the information recording medium can be distributed or sold.

The program is installed in the non-transitory information recording medium such as a hard disk, a solid state drive, a flash memory, and an EEPROM included in the computer. Then, the computer achieves an information processing device according to the present embodiment. In general, a central processing unit (CPU) of the computer reads the program from the information recording medium into a random access memory (RAM) under management by an operating system (OS) of the computer, and then interprets and executes a code included in the program. However, in an architecture in which the information recording medium can be mapped in a memory space accessible by the CPU, explicit loading of the program into the RAM may not be needed. Note that various types of information needed in a process of execution of the program may be temporarily recorded in the RAM.

Furthermore, as described above, the computer desirably includes a graphics processing unit (GPU) for performing various image processing calculations at a high speed. By using the GPU and a library such as TensorFlow, a learning function and a classification function in various types of artificial intelligence processing can be used under control of the CPU.

Note that, instead of achieving the information processing device according to the present embodiment by a general-purpose computer, the information processing device according to the present embodiment can also be formed by using a dedicated electronic circuit. In this aspect, the program can also be used as a material for generating a wiring drawing, a timing chart, and the like of the electronic circuit. In such an aspect, the electronic circuit that satisfies specifications determined in the program is formed of a field programmable gate array (FPGA) and an application specific integrated circuit (ASIC), the electronic circuit functions as a dedicated apparatus that achieves a function determined in the program, and achieves the information processing device according to the present embodiment.

Hereinafter, in order to facilitate understanding, description is given by assuming an aspect in which the tomographic image processing device 101 is achieved by a program executed by a computer.

The acquirer 111 acquires a moving image in which a cross section of a living body is captured via a light-receiving surface of a puncture member that punctures the living body.

Herein, the puncture member in the present embodiment is a puncture member that is a thin wire acquired by bundling optical fibers, and the puncture member punctures a living body in a longitudinal direction of the thin wire, and one of stumps of the thin wire is a light-receiving surface for capturing a cross section of the living body. When the puncture member punctures a living body, the longitudinal direction of the thin wire is a depth direction of the living body, that is, a direction from the outside of the living body toward the inside of the living body. When the puncture member punctures skin of a living body in a substantially vertical direction, a direction of puncturing is a so-called Z-axis direction, but control can also be performed in such a way that the puncture member obliquely punctures the skin of the living body, or obliquely punctures the skin of the living body and then punctures the inside of the living body in substantially parallel with the skin.

Figure 2:
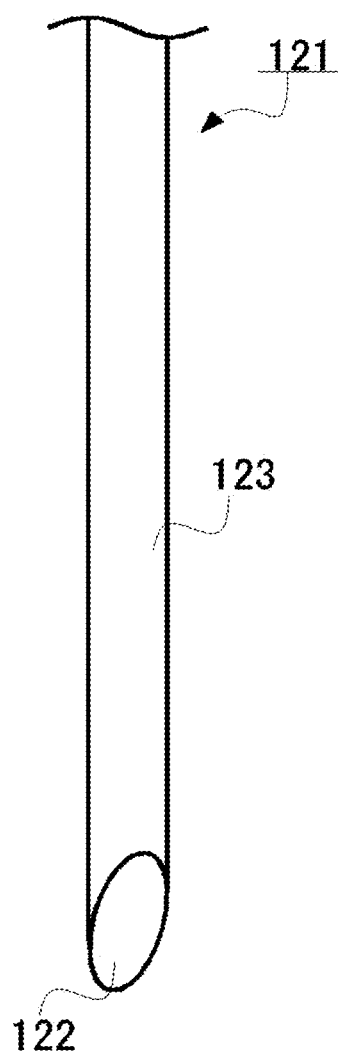
FIG. 2 is an explanatory drawing illustrating an appearance of a puncture member.
Figure 3:
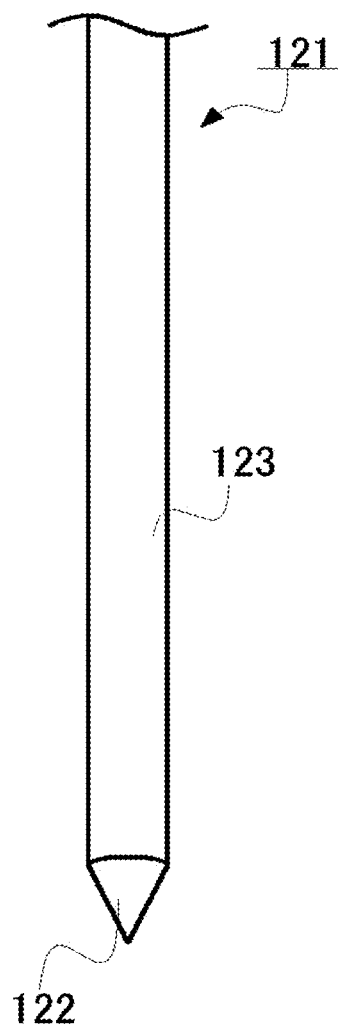
FIG. 3 is an explanatory drawing illustrating an appearance of the puncture member.

FIGS. 2 and 3 are explanatory drawings illustrating an appearance of the puncture member. Hereinafter, description is given with reference to FIGS. 2 and 3.

In these drawings, two kinds of a puncture member 121 are illustrated. In the both cases, a light-receiving surface 122 of the puncture member 121 is provided on a stump of a thin wire 123.

As the thin wire 123, for example, an imaging fiber being acquired by bundling approximately ten thousand optical fibers, having a diameter of approximately 0.35 mm (several hundreds of μm), and having approximately ten thousand pixels can be used. For example, existing articles on the market include HDIG of SUMITA OPTICAL GLASS, Inc., FIGH of Fujikura Ltd., and the like. Specifications of the imaging fibers can be appropriately changed according to a use.

Since the light-receiving surface 122 side of the puncture member 121 has a needle shape by polishing the stump of the thin wire 123 being extremely thin, the puncture member 121 easily punctures a living body, is minimally invasive, and rarely causes bleeding. Therefore, a time change in tissue by repeatedly performing puncturing at time intervals can also be observed.

Figure 4:
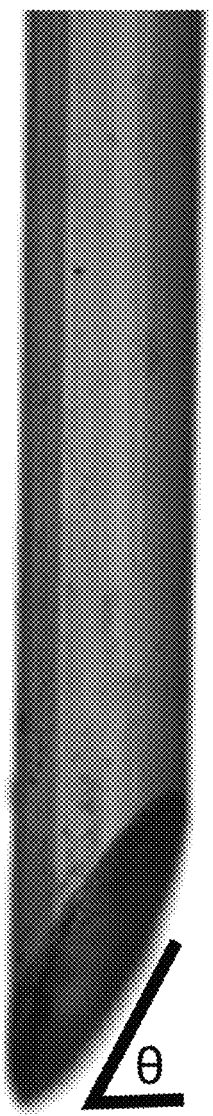
FIG. 4 is a drawing representative picture in which a tip of the puncture member having a bamboo spear shape is captured in a gray scale.
Figure 5:
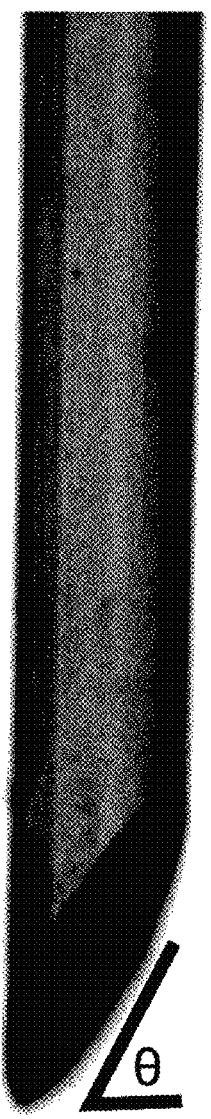
FIG. 5 is an explanatory drawing acquired by performing monochrome binarization on the drawing representative picture in which the tip of the puncture member having the bamboo spear shape is captured.

FIG. 4 is a drawing representative picture in which a tip of the puncture member having a bamboo spear shape is captured in a gray scale. FIG. 5 is an explanatory drawing acquired by performing monochrome binarization on the drawing representative picture in which the tip of the puncture member having the bamboo spear shape is captured. In the puncture member 121 illustrated in these drawings, the light-receiving surface 122 is formed in a planar shape having a predetermined angle formed with a longitudinal direction of the thin wire 123. In the examples illustrated in FIGS. 4 and 5, an angle θ formed between the light-receiving surface 122 and the longitudinal direction of the thin wire 123 is 60 degrees, and a tip on the light-receiving surface 122 side of the thin wire 123 is acute. When the thin wire 123 is compared to a bamboo, the light-receiving surface 122 being one of stumps of the thin wire 123 is a cross section acquired by obliquely cutting a tip of the bamboo, and the periphery of the stump of the puncture member 121 has a bamboo spear shape. When a shape of a cross section at a right angle to the longitudinal direction of the thin wire 123 is substantially circular, that is, when the thin wire 123 is a round wire, a shape of the light-receiving surface 122 is substantially elliptic.

Figure 6:
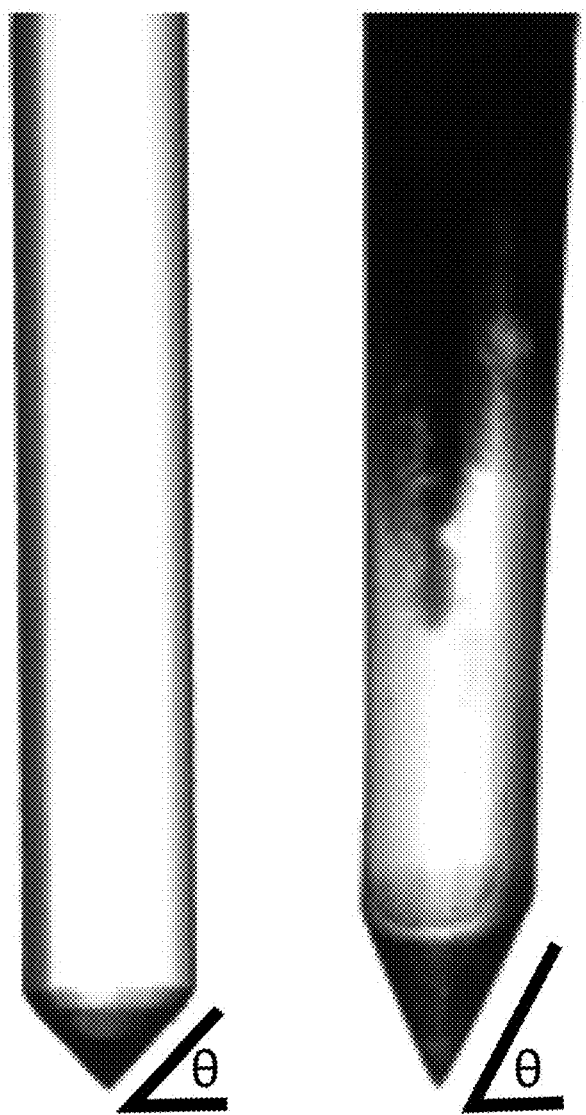
FIG. 6 is a drawing representative picture in which a tip of the puncture member having a round pencil shape is captured in a gray scale.
Figure 7:
FIG. 7 is an explanatory drawing acquired by performing monochrome binarization on the drawing representative picture in which the tip of the puncture member having the round pencil shape is captured.

FIG. 6 is a drawing representative picture in which a tip of the puncture member having a round pencil shape is captured in a gray scale. FIG. 7 is an explanatory drawing acquired by performing monochrome binarization on the drawing representative picture in which the tip of the puncture member having the round pencil shape is captured. In the puncture member 121 illustrated in these drawings, the light-receiving surface 122 is formed in a conical surface shape in which the longitudinal direction of the thin wire 123 is a central axis direction. In the examples illustrated in FIGS. 6 and 7, an angle θ formed between a conical surface of the light-receiving surface 122 and the longitudinal direction of the thin wire 123 is 45 or 60 degrees, and a tip of the light-receiving surface of the thin wire 123 has a right-angled needle shape. When the thin wire 123 is compared to a round pencil, the light-receiving surface 122 being one of stumps of the thin wire 123 corresponds to a conical exposed surface with a lead exposed by shaving the tip of the round pencil, and the periphery of the stump of the puncture member 121 has a round pencil shape. When the thin wire 123 is a round wire, a shape acquired by developing the light-receiving surface 122 into a planar shape is a substantially fan shape.

In addition, as the light-receiving surface 122 of the puncture member 121, various aspects can be adopted in such a way as to adopt a polygonal conical surface shape and adopt a shape provided with two surfaces like a tip of a precision slotted screwdriver. Further, an angle formed between the light-receiving surface 122 and the longitudinal direction of the thin wire 123 can also be appropriately changed.

An opposite end being opposite to the light-receiving surface 122 side of the thin wire 123 of the puncture member 121 is installed on an object lens side of a confocal microscopic endoscope unit, and the stump on the light-receiving surface 122 side functions as an endoscopic probe.

In the confocal microscopic endoscope, when the thin wire 123 is irradiated with laser light via the object lens by a multicolor laser system (wavelength of 475 nm/561 nm), the laser light passes through the thin wire 123 and is irradiated as excitation light from the light-receiving surface 122 into tissue of a punctured living body.

For example, when a Fluorescent Ubiquitination-based Cell Cycle Indicator (Fucci) system in which a fluorescent wavelength changes in a state of a cell cycle is introduced in advance for a cancer cell, red fluorescence is emitted from a cell nucleus in a G1 cycle and green fluorescence is emitted from a cell nucleus in an S/G2/M cycle, based on the excitation light.

The emitted fluorescence reaches the object lens of the microscopic endoscope via the light-receiving surface 122 and the thin wire 123, and is converted into an electric signal by a photomultiplier tube, and a scene of a captured cross section of a living body can be acquired in a form of an image file. By continuously performing capturing during puncturing with the puncture member 121 at a substantially uniform speed, a scene of the cross section of the living body can be acquired in a form of a moving image. In the moving image, tissue (such as a cell, a cell nucleus, and a cell organelle) of the living body is captured in a direction reverse to a direction in which the puncture member 121 travels.

As described above, a shape of the light-receiving surface 122 is an ellipse or a conical surface (fan shape), but the opposite end of the thin wire 123 is circular. This is observed by a microscopic endoscope.

Figure 8:
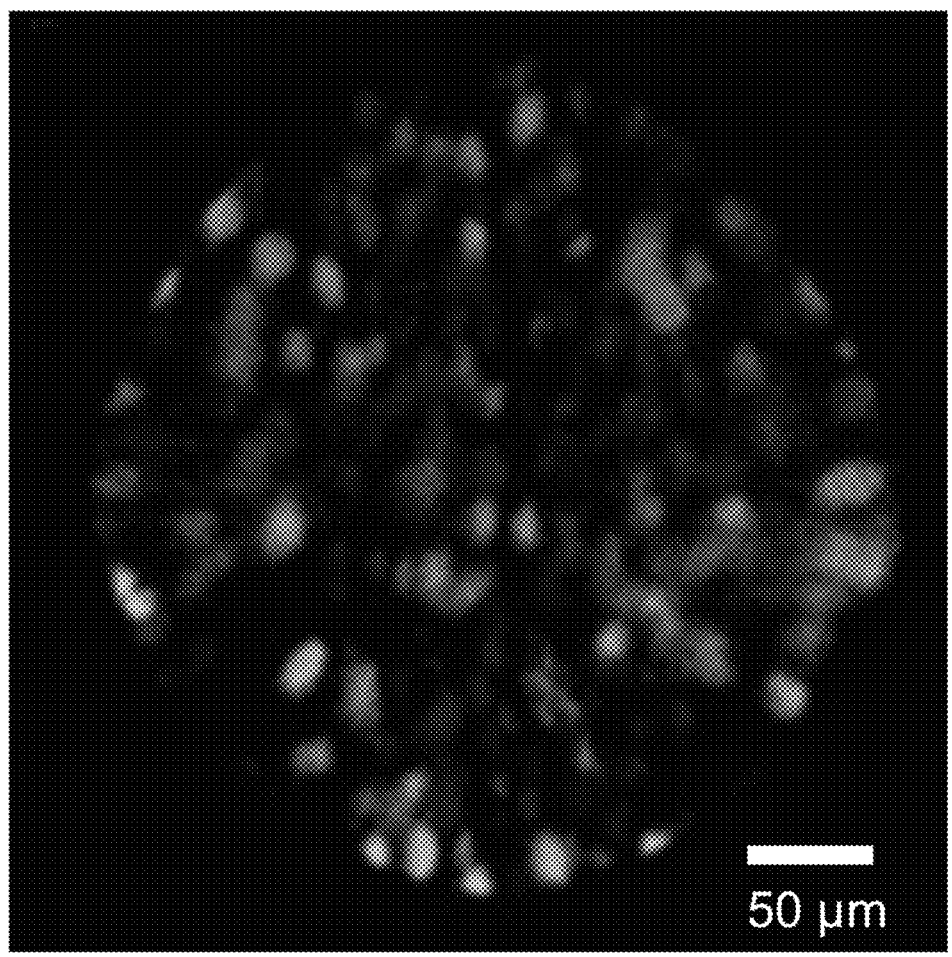
FIG. 8 is a drawing representative picture indicating, in a gray scale, an example of an image captured by a microscopic endoscope.
Figure 9:
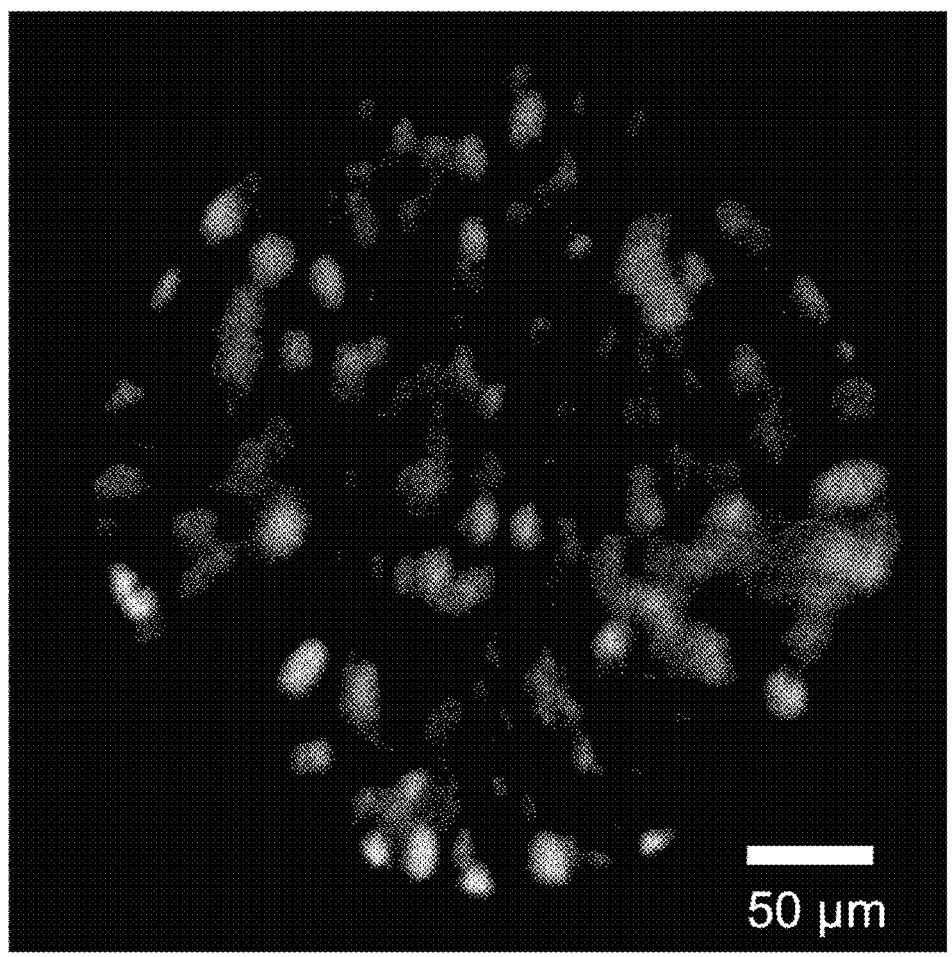
FIG. 9 is an explanatory drawing acquired by performing monochrome binarization on the drawing representative picture indicating the example of the image captured by the microscopic endoscope.

FIG. 8 is a drawing representative picture indicating, in a gray scale, an example of an image captured by a microscopic endoscope. FIG. 9 is an explanatory drawing acquired by performing monochrome binarization on the drawing representative picture indicating the example of the image captured by the microscopic endoscope. As illustrated in these drawings, light received by the light-receiving surface 122, that is, the image acquired by the microscopic endoscope is projected in a circular shape.

Figure 10:
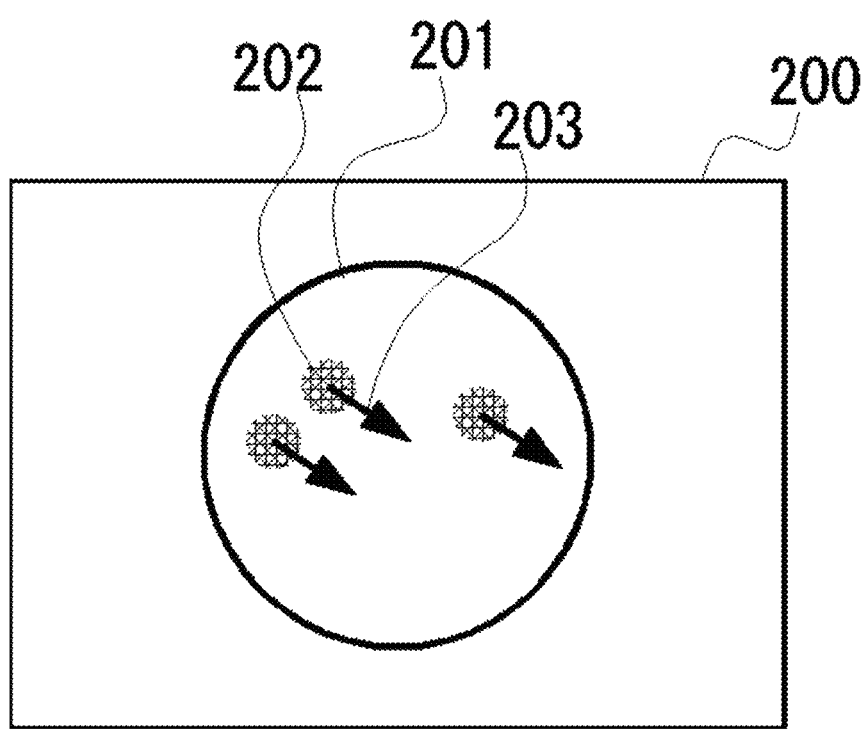
FIG. 10 is an explanatory drawing schematically illustrating an image captured by the puncture member having the bamboo spear shape.

FIG. 10 is an explanatory drawing schematically illustrating an image captured by the puncture member having the bamboo spear shape. FIG. 10 illustrates the image corresponding to one frame of a moving image acquired from a microscopic endoscope by using the puncture member 121 having the bamboo spear shape. A shape of a cross section 201 of a living body in a captured frame 200 is circular, and a movement direction 203 in which tissue 202 of the living body indicated by hatching in FIG. 10 moves in the moving image corresponds to a direction reverse to a traveling direction of the puncture member 121.

In FIG. 10, the puncture member 121 having the bamboo spear shape is assumed, and thus each tissue 202 is expected to move in parallel in substantially the same direction in a field of view unless each tissue 202 is not caught on the puncture member 121, not deformed, not ruptured, not adhering to the light-receiving surface 122, and the like.

As described above, a shape of the light-receiving surface 122 is an ellipse in the puncture member 121 having the bamboo spear shape and is a fan shape in the puncture member 121 having the round pencil shape, but is deformed into the circular shape in the frame of the moving image. Thus, the corrector 112 performs image correction in such a way that a direction in which the tissue 202 of the living body moves in the moving image is parallel.

In the puncture member 121 having the bamboo spear shape, directions in which the tissue 202 of the living body is expected to move in the moving image are parallel to each other, and thus the corrector 112 can perform image correction by obtaining a coordinate value of each pixel of each frame of the acquired moving image, and performing projecting with the obtained coordinate value as each value of orthogonal coordinates.

Figure 11:
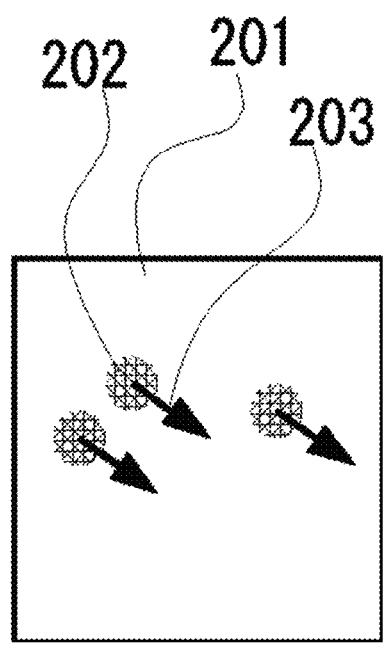
FIG. 11 is an explanatory drawing illustrating a result of performing image correction on the image captured by the puncture member having the bamboo spear shape.

FIG. 11 is an explanatory drawing illustrating a result of performing image correction on the image captured by the puncture member having the bamboo spear shape. As illustrated in FIG. 11, the image correction for the puncture member 121 having the bamboo spear shape corresponds to image correction that sets desired size and position.

Figure 12:
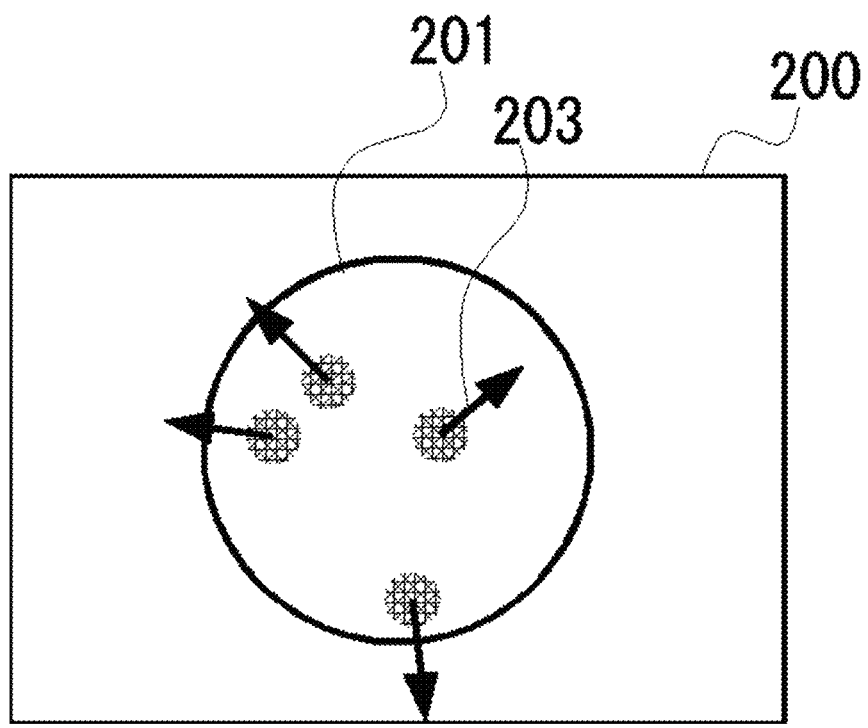
FIG. 12 is an explanatory drawing schematically illustrating an image captured by the puncture member having the round pencil shape.

Hereinafter, a case of the puncture member 121 of the round pencil is considered. FIG. 12 is an explanatory drawing schematically illustrating an image captured by the puncture member having the round pencil shape. FIG. 12 illustrates the image corresponding to one frame of a moving image acquired from a microscopic endoscope by using the puncture member 121 having the round pencil shape. Similarly to the case of the puncture member 121 having the bamboo spear shape, a shape of the cross section 201 of the living body in the captured frame 200 is circular, and the movement direction 203 in which the tissue 202 of the living body indicated by hatching in FIG. 12 moves in the moving image corresponds to a direction reverse to a traveling direction of the puncture member 121.

In FIG. 12, the puncture member 121 having the round pencil shape is assumed, and thus each tissue 202 is expected to dispersedly move in a direction spreading from the center (corresponding to a pole of a conical shape) of the cross section 201 having a circular shape in a field of view.

The corrector 112 performs image correction of each frame of the acquired moving image, based on a shape of the light-receiving surface 122.

Further, in the puncture member 121 having the round pencil shape, a direction in which the tissue 202 of the living body is expected to move in the moving image is a direction spreading from the center (pole), and thus the corrector 112 can perform image correction by determining a pole common to each frame of the acquired moving image, obtaining, by a pole coordinate system based on the determined pole, a coordinate value of pole coordinates of each pixel of each frame of the acquired moving image, and performing projecting with the obtained coordinate value of the pole coordinates as each value of orthogonal coordinates.

A simplest method for determining a pole is a technique for determining a substantially circular shape since the periphery of the cross section 201 in each frame is the substantially circular shape, and setting the center of the substantially circular shape as a pole. The other technique is described below.

Figure 13:
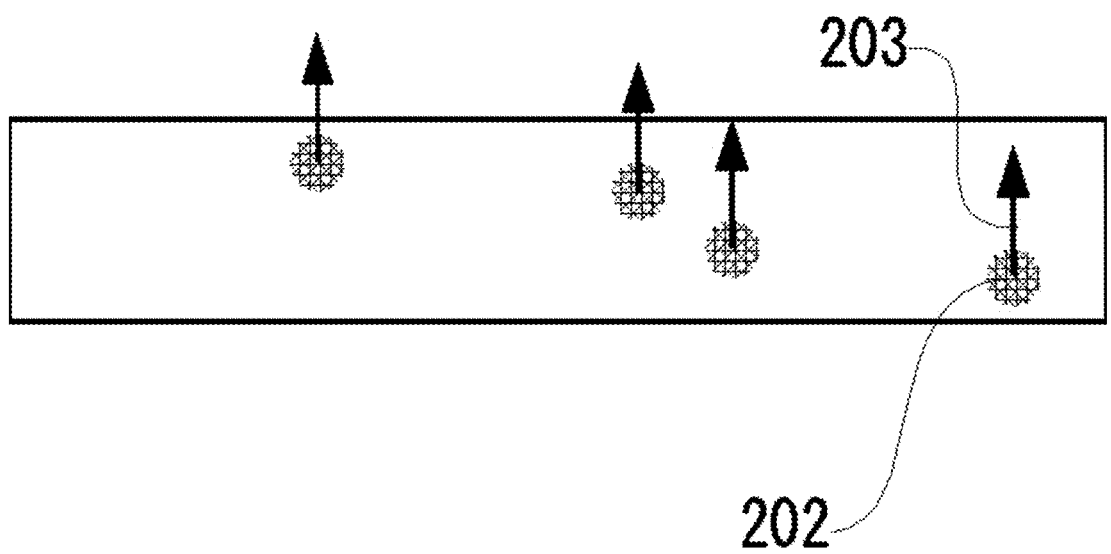
FIG. 13 is an explanatory drawing illustrating a result of performing image correction on the image captured by the puncture member having the round pencil shape.

A coordinate value of pole coordinates is expressed by a distance from a pole and an angle from a predetermined direction extending from the pole. FIG. 13 is an explanatory drawing illustrating a result of performing image correction on the image captured by the puncture member having the round pencil shape. As illustrated in FIG. 13, a distance and an angle of each point are projected as they are as each value of orthogonal coordinates.

Since the tissue 202 of the living body is expected to radially move around the pole, when the projection as described above is performed, a coordinate value of the orthogonal coordinates on a side on which the distance is projected gradually increases, whereas a coordinate value of the orthogonal coordinates on a side on which the angle is projected is fixed.

Thus, in each frame of the moving image after the projection, the tissue 202 of the living body is expected to move in the movement directions 203 parallel to each other.

Note that distortion of the image is great in the vicinity of the pole, and thus the vicinity of the pole may be removed from a target of the projection.

Note that the corrector 112 desirably performs noise removal by using a Gaussian filter and the like.

Then, the tracker 113 tracks a candidate for a picture of the tissue 202 of the living body that satisfies a desired tracking condition in the moving image on which the image correction is performed.

As described above, in the present embodiment, a fluorescent probe is given to tissue desired to be observed ("tissue" is a general term including a cell, an organelle, an extracellular matrix, a biomolecular structure, and the like), the tissue desired to be observed is caused to generate fluorescent protein such as Fucci, and the like, and thus the tissue is caused to emit fluorescence.

Thus, as a tracking condition, a condition that a color of a picture is the same as a color of fluorescence (such as a wavelength of fluorescence) emitted from the tissue and has a fixed luminance value, a condition that a size of a picture formed of a region of the color matches a range of a size of assumed tissue, a condition that a shape of a picture formed of a region of the color matches a shape (for example, a substantially circular shape) of assumed tissue, a combination thereof, and the like can be adopted.

Note that an image processing technique that satisfies the tracking conditions may be used as it is. For example, a technique such as scale-invariant feature transform (SIFT) may be applied, and a feature point corresponding to the desired tissue 202 of the living body may be extracted and tracked.

Then, only a picture that satisfies a tracking condition is set as a candidate, and a picture that does not satisfy the tracking condition such as a picture of a region of a color different from that of assumed fluorescence or a region having the same color as that of assumed fluorescence but not matching size and shape is not set as a target in the following processing.

In other words, the tracker 113 does not set, as a target of tracking, a picture of tissue that does not satisfy a desired tracking condition.

In this way, the tissue 202, dust, and the like that leave the living body and adhere to the light-receiving surface 122 can be handled as an error.

When tracking is performed on a candidate for a picture of the desired tissue 202 of the living body in each frame of the moving image, the estimator 114 estimates, based on a movement vector of the tracked candidate, a representative vector in the moving image on which the image correction is performed.

The representative vector is a vector just in an opposite direction to a puncture vector in which the puncture member 121 puncturing the living body moves.

It is expected that the movement vector of the candidate has a fixed size in a fixed direction while the puncture member 121 punctures the living body at a fixed speed, but a reduction in friction, deformation, cramp, and the like may occur, and the size of the movement vector may change. However, it is conceivable that the movement vector generally has the same direction.

Thus, as a direction of the representative vector in the moving image, a mode and an average value of the direction of the movement vector of each candidate can be adopted.

Next, the extractor 115 extracts a candidate similar to the estimated representative vector. Herein, the "candidate similar to the representative vector" means a candidate in which a direction of the representative vector and a direction of the movement vector of the candidate fall within a predetermined allowable range.

By not setting, as a target of extraction, a candidate that does not fall within the allowable range, for example, the tissue 202, dust, and the like that leave the living body and move while sliding on the puncture member 121 can be handled as an error.

Then, the calculator 116 calculates, based on a drawing position in a frame in which the picture of the extracted candidate is drawn in the moving image and an order of the frame, an arrangement position in which the picture of the extracted candidate needs to be arranged.

Lastly, the generator 117 generates a pseudo tomographic image of the living body by drawing the picture of the extracted candidate in the calculated arrangement position.

An order of a frame is a numerical value corresponding to a depth at which the puncture member 121 punctures a living body, and tissue corresponding to a picture is present in a deeper portion of the living body as the order in which the picture appears in the frame is later. Therefore, a position in a depth direction of an arrangement position can be determined based on an order in which a picture appears in a frame.

Further, in the moving image, the picture of the tissue 202 of the living body is expected to move in the same direction as a direction of the representative vector. Thus, a coordinate axis orthogonal to the direction of the representative vector is considered in each frame of the moving image, and a coordinate value of the picture in the coordinate axis can be adopted in a direction orthogonal to the depth of the arrangement position.

In fact, the picture of the tissue 202 of the living body may deviate from the direction of the representative vector within the predetermined allowable range and move, and thus a coordinate value of the picture in the coordinate axis orthogonal to the direction of the representative vector can be obtained based on a position of the picture at a specific point in time such as, for example, a point in time at which tracking of the picture of the tissue 202 of the living body starts, and the coordinate value can be set as a position in a direction orthogonal to the depth direction of the arrangement position.

Further, for calculation of an arrangement position of a picture, any of a position of the picture in a frame in which tracking starts, a position of the picture in a frame during tracking, and a position of the picture in a frame in which tracking ends may be selected, or processing of leveling may be appropriately performed.

The calculator 116 may perform position correction of the calculated arrangement position according to a direction of the representative vector. For example, since distortion resulting from an angle difference between the light-receiving surface 122 and the longitudinal direction of the thin wire 123 occurs, correction is performed when an arrangement position is calculated. For example, when an angle difference is 60 degrees, distortion is 1:2, and thus an arrangement position at a double distance in a longitudinal direction in a moving image may be determined. The correction can be performed with any correction value.

In addition, expansion and reduction can be performed along a direction of a representative vector in such a way that a distribution when a tissue slice of an extracted sample of another individual being created by an existing technique is observed by a microscope matches a distribution of an arrangement position being calculated this time. When both of the distributions match, an arrangement condition is satisfied.

Further, a direction and a size of a representative vector (puncture vector) may change during puncturing of the puncture member 121. In this case, position correction is performed on an arrangement position in consideration of the change. At this time, a correction technique when a panoramic picture is captured by rotating a camera of a smartphone and the like with a hand, and the like can also be applied.

As a picture of a candidate being drawn in a calculated arrangement position by the generator 117, most simply, a picture at a specific point in time such as a point in time at which tracking starts can be adopted, or an average image of a picture during tracking may be drawn in the calculated arrangement position.

A technique as described below can also be adopted in order to determine a position of a pole in a case of the puncture member 121 having the round pencil shape.

First, a position of a pole is temporarily determined, and processing by the corrector 112, the tracker 113, the estimator 114, and the extractor 115 is performed.

Then, all directions of a movement vector of a picture of an extracted candidate are expected along one axis of orthogonal coordinates in an allowable range.

Thus, the position of the pole is corrected in such a way that an error in the direction is further reduced, that is, the direction of the movement vector of the picture of the candidate is set closer to a parallel direction.

Even when the center of the conical shape of the tip of the puncture member 121 having the round pencil shape is deviated, and the like, a pole can be more accurately determined by repeating the processing.

Hereinafter, control of tomographic image processing performed by the tomographic image processing device according to the present embodiment is described in detail. In the present processing, description is given with one example of the various aspects described above as a representative example, but various aspects can be achieved by changing details of each processing according to the description described above.

Figure 14:
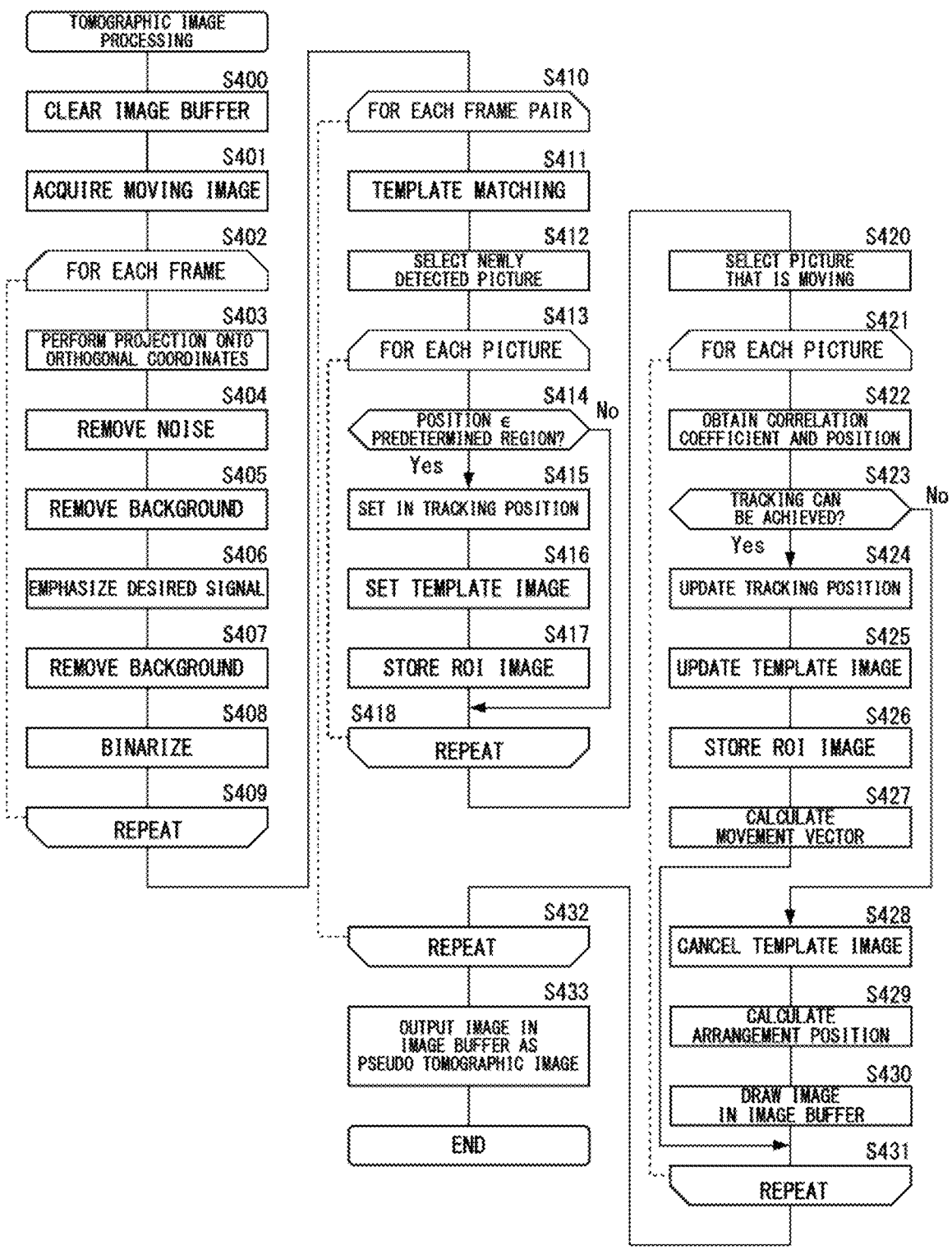
FIG. 14 is a flowchart illustrating control of tomographic image processing according to the present embodiment.

FIG. 14 is a flowchart illustrating the control of the tomographic image processing according to the present embodiment. Hereinafter, description is given with reference to FIG. 14.

First, the tomographic image processing device 101 clears an image buffer for a tomographic image (step S400).

Next, the tomographic image processing device 101 acquires a moving image in which a cross section of a living body is captured via the light-receiving surface 122 of the puncture member 121 that punctures the living body (step S401).

Then, the tomographic image processing device 101 repeats the following processing for each frame of the moving image (step S402).

In other words, the tomographic image processing device 101 resizes each frame into a predetermined processing size while an aspect ratio is maintained, and performs projection onto orthogonal coordinates, based on a shape of the light-receiving surface (step S403).

Then, the tomographic image processing device 101 applies a Gaussian filter to the projected image, removes noise (step S404), then takes a difference by applying a rough Gaussian filter and a fine Gaussian filter, thus removes a background, and emphasizes a signal (step S405).

Furthermore, the tomographic image processing device 101 applies a Laplacian of Gaussian (LoG) filter and the like, and emphasizes a signal corresponding to a shape and a size of desired tissue (step S406).

Moreover, the tomographic image processing device 101 takes a difference again by applying the rough Gaussian filter and the fine Gaussian filter, thus removes the background, and emphasizes the signal (step S407).

Subsequently, the tomographic image processing device 101 performs binarization, and extracts a region of the signal (step S408). In this way, a position of a picture of the desired tissue is determined.

When repetition for each frame ends (step S409), the tomographic image processing device 101 repeats the following processing for a pair (pair of a previous frame and a current frame) of two adjacent frames (step S410).

In other words, the tomographic image processing device 101 compares the previous frame and the current frame by template matching (step S411), selects each picture of tissue newly detected from the current frame (without a template image being set) (step S412), and repeats the following processing for each picture (step S413).

In other words, when a position of the picture in the current frame is located in a predetermined region not being around a field of view (step S414; Yes), the tomographic image processing device 101 considers that a picture needed to be tracked newly appears, and sets a position of the picture in a tracking position (step S415), sets a template image, based on the picture (step S416), and repeats (step S418) processing of storing a region of interest (ROI) image (color channel image) for being attached to a pseudo tomographic image, based on the picture in the current frame and the original frame of the moving image (step S417).

On the other hand, when a picture needed to be tracked does not newly appear (step S414; No), the processing proceeds to step S418.

Next, the tomographic image processing device 101 selects each picture of the tissue moving within an assumed movement amount between the previous frame and the current frame as a result of the comparison of the template matching (step S420), and repeats the following processing for each picture (step S421).

In other words, the tomographic image processing device 101 obtains a correlation coefficient and a position of the previous frame and the current frame of the picture (step S422).

When the obtained correlation coefficient is equal to or more than a threshold value, and the position is located in the predetermined region not being around the field of view, tracking of the picture can be achieved (step S423; Yes), the tomographic image processing device 101 updates a tracking position, based on the picture in the current frame (step S424), also updates the template image (step S425), and stores an ROI image (color channel image) for being attached to a pseudo tomographic image, based on the picture in the current frame and the original frame of the moving image (step S426).

Furthermore, the tomographic image processing device 101 calculates a movement vector, based on the position of the picture in the previous frame and the position of the picture in the current frame (step S427), and the processing proceeds to step S431.

On the other hand, when the picture cannot be tracked and is lost (step S423; No), the tomographic image processing device 101 cancels setting of the template image of the picture (step S428), and ends tracking.

Then, the tomographic image processing device 101 calculates an arrangement position, based on an order of the previous frame, a position of the picture in the previous frame, the movement vector of the picture, a representative vector (puncture vector), and the like (step S429), and draws, in the calculated arrangement position, an average image based on the ROI image stored for the tissue in the image buffer for the tomographic image by correcting the arrangement position and distortion of the picture being derived from a light-receiving surface shape (step S430).

When repetition for the picture moving between the previous frame and the current frame ends (step S431), and repetition for all pairs of the frames ends (step S432), the tomographic image processing device 101 outputs the image drawn in the image buffer as a pseudo tomographic image of the living body (step S433), and ends the present processing.

Note that an average (corresponding to a representative vector) of a calculated movement vector can be obtained, tracking for a picture of a movement vector having a great deviation from the average can end, and drawing in an image buffer can also be omitted (not illustrated) without calculating an arrangement position.

For example, when dust adhering/remaining onto the light-receiving surface 122 is great, an influence of a picture that is not linked to movement of the puncture member 121 can be removed by adopting the technique as described above.

Experimental Results

A cancer-bearing model in which transplantation of a cultured cancer cell (human fibrosarcoma cell: HT1080) is performed under skin of an immunodeficient mouse (Balb/cAjcl nu/nu) and a cancer-bearing model animal in which allogeneic transplantation of a cultured cancer cell (mouse colorectal cancer cell: Colon 26) is performed under skin of a mouse (Balb/cAjcl) were prepared.

A Fucci system in which a fluorescent wavelength changes in a state of a cell cycle is introduced for a cancer cell, and red fluorescence is emitted from a cell nucleus in a G1 cycle and green fluorescence is emitted from a cell nucleus in an S/G2/M cycle.

At a time of puncture imaging, an inhalation anesthesia procedure was performed on a mouse, a tumor was retained by a retainer, and a puncture for puncturing with an endoscopic probe was made by puncturing skin of a tumor surface with an injection needle.

While the endoscopic probe was controlled by an auto manipulator and punctured the tumor surface on a puncture side (skin side) and an opposite side at a fixed speed of 4 mm/min, continuous capturing was performed at a capturing speed of 18 fps (18 images per second), and clear fluorescence derived from a cell nucleus was detected in tumor tissue.

At this time, since invasion due to imaging was small, a puncture mark was extremely small, and bleeding was not seen, repetitive imaging for a long period was achieved.

A fluorescent captured image acquired by microscopic endoscope imaging was output in a moving image form by continuous capturing, and a (red or green) cell nucleus moving against a traveling direction of the endoscopic probe was captured.

A pseudo tomographic image construction program was created with, as a linchpin, a tracking program of OpenCV being a computer vision library of an open source, and tracking of each object (each cell) was achieved by causing an object (a cell nucleus in this experimental example) in a microscopic endoscope captured image to be recognized for each channel (a recognized condition was defined by various parameters such as size).

At this time, design was performed in such a way that a vector value was given to each from movement of a recognized cell nucleus and an average value thereof was calculated for each frame.

By determining a vector value (puncture vector) of the endoscopic probe, based on the vector average value (representative vector), how the endoscopic probe traveled (direction and speed) with respect to punctured tissue during reconstruction of a tomographic image was estimated, and an arrangement position was appropriately corrected accordingly.

By detecting deviation from a value (stationary state) in which a vector value of an object is close to 0 or a vector value of the endoscopic probe, a nonspecific fluorescent signal and a cell adhering to an optical fiber surface were removed.

On the framework, a pseudo tomographic image was reconstructed by projecting a recognized cell nucleus (average image during tracking) onto a recognized initial point.

Figure 15:
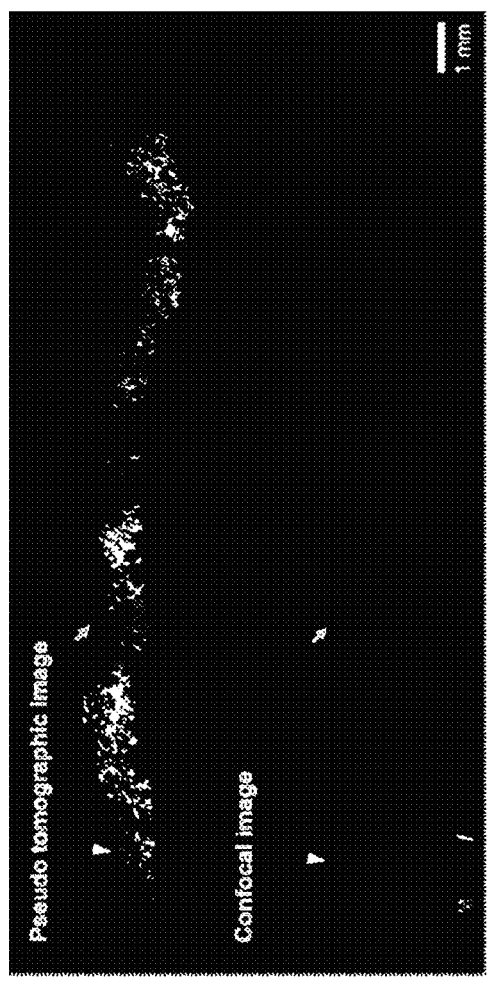
FIG. 15 is a drawing representative picture in which a pseudo tomographic image according to the present embodiment and an extracted sample image according to a conventional technique are compared in a gray scale.
Figure 16:
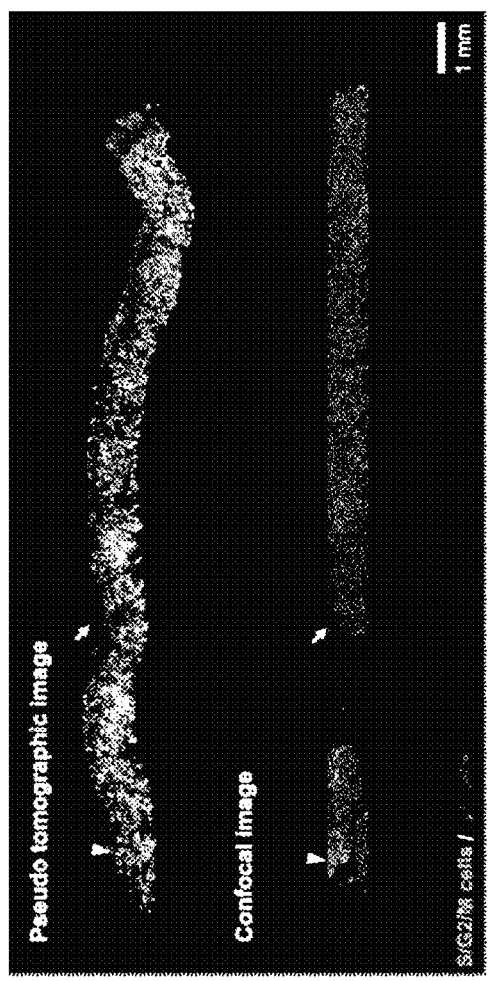
FIG. 16 is an explanatory drawing acquired by performing monochrome binarization on the drawing representative picture in which the pseudo tomographic image according to the present embodiment and the extracted sample image according to a conventional technique are compared.

FIG. 15 is a drawing representative picture in which a pseudo tomographic image according to the present embodiment and an extracted sample image according to a conventional technique are compared in a gray scale. FIG. 16 is an explanatory drawing acquired by performing monochrome binarization on the drawing representative picture in which the pseudo tomographic image according to the present embodiment and the extracted sample image according to a conventional technique are compared. When the pseudo tomographic images on an upper row in the drawings and the extracted sample images (confocal images) on a lower row are compared, it is clear that a normal fluorescent microscopic image in which a tissue slice of an extracted sample is observed and a similar pseudo tomographic image are acquired. Note that, since an arrangement position is corrected in consideration of a change in a representative vector (puncture vector) in the drawings, a pseudo tomographic image has a curved band shape.

Figure 17:
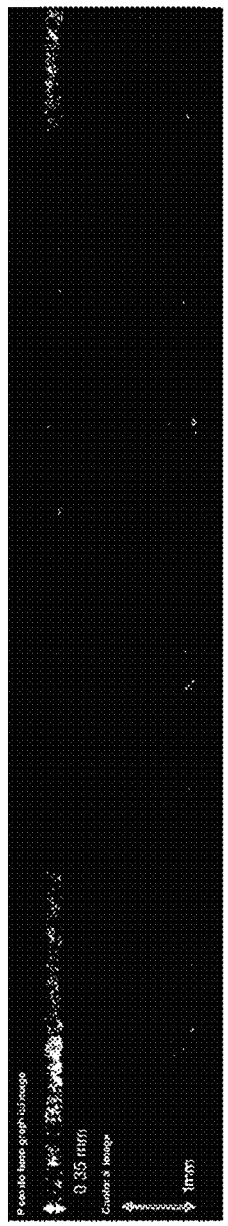
FIG. 17 is a drawing representative picture in which a pseudo tomographic image according to the present embodiment and an extracted sample image according to a conventional technique are compared in a gray scale.
Figure 18:
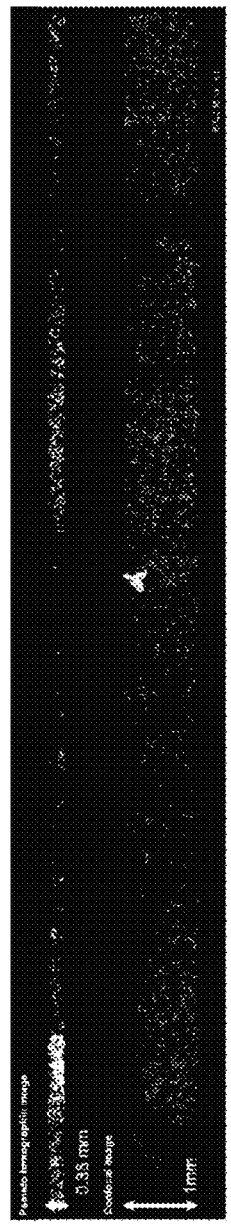
FIG. 18 is an explanatory drawing acquired by performing monochrome binarization on the drawing representative picture in which the pseudo tomographic image according to the present embodiment and the extracted sample image according to a conventional technique are compared.

FIG. 17 is a drawing representative picture in which a pseudo tomographic image according to the present embodiment and an extracted sample image according to a conventional technique are compared in a gray scale. FIG. 18 is an explanatory drawing acquired by performing monochrome binarization on the drawing representative picture in which the pseudo tomographic image according to the present embodiment and the extracted sample image according to a conventional technique are compared. Since it is assumed that a representative vector (puncture vector) is fixed in the drawings, a pseudo tomographic image has a band shape without a curve.

Note that the present aspect can be used without being defined in a setup form of an optical fiber and a microscopic endoscope.

Figure 19:
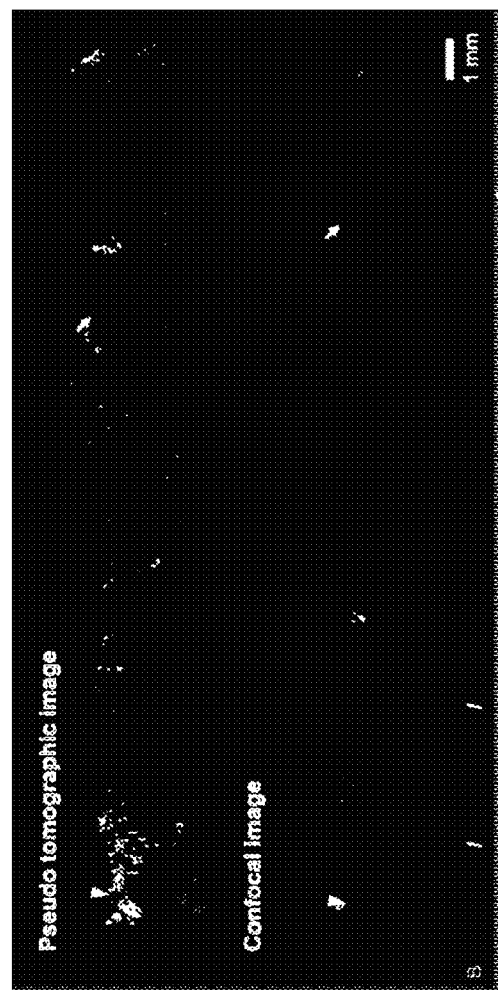
FIG. 19 is a drawing representative picture in which a pseudo tomographic image according to the present embodiment and an extracted sample image according to a conventional technique are compared in a gray scale.
Figure 20:
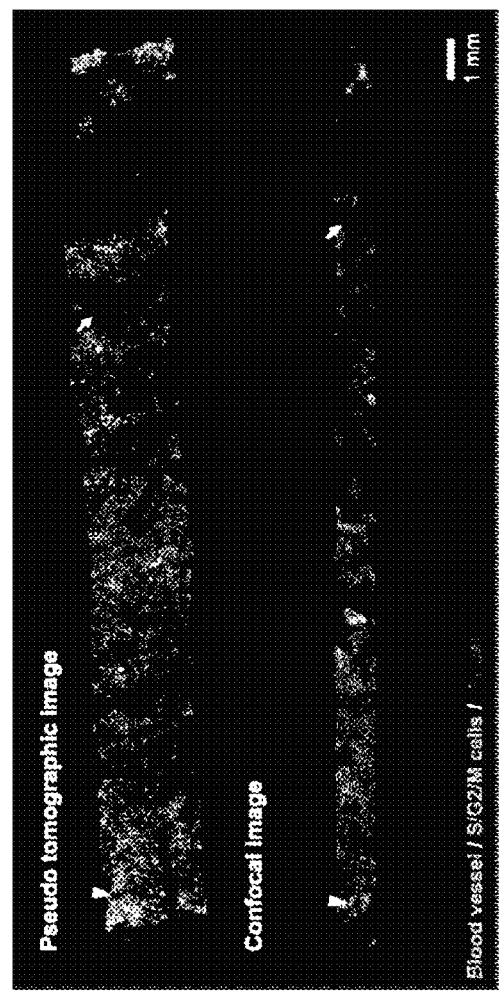
FIG. 20 is an explanatory drawing acquired by performing monochrome binarization on the drawing representative picture in which the pseudo tomographic image according to the present embodiment and the extracted sample image according to a conventional technique are compared.

For example, a multicolor laser system of a confocal microscopic unit can be increased, and simultaneous imaging of three or more colors can be achieved by increasing a laser of 430 nm, 630 nm, and the like. FIG. 19 is a drawing representative picture in which a pseudo tomographic image according to the present embodiment and an extracted sample image according to a conventional technique are compared in a gray scale. FIG. 20 is an explanatory drawing acquired by performing monochrome binarization on the drawing representative picture in which the pseudo tomographic image according to the present embodiment and the extracted sample image according to a conventional technique are compared. Similarly in the drawings, a normal fluorescent microscopic image in which a tissue slice of an extracted sample is observed and a similar pseudo tomographic image are acquired.

Further, a diameter of an optical fiber can be changed from 0.2 mm to 0.5 mm, and can be changed according to a target tissue and a use from a viewpoint of a field of view (FOV) and invasiveness.

In addition, a tip shape of an endoscopic probe can also be changed by adjusting a polishing manner of an optical fiber. In the experimental example described above, an optical fiber is polished into a bamboo spear shape, but can also be polished into a pencil shape and a polygonal pyramid and at any inclination angle. Further, even when an optical fiber is polished into a dome shape, the scope of the present embodiment can be achieved by performing projection according to the shape.

CONCLUSION

A tomographic image processing device according to the present embodiment including:

an acquirer that acquires a moving image in which a cross section of a living body is captured via a light-receiving surface of a puncture member that punctures the living body;

a corrector that performs image correction of each frame of the acquired moving image, based on a shape of the light-receiving surface;

a tracker that tracks a candidate for a picture of tissue of the living body that satisfies a desired tracking condition in the moving image on which the image correction is performed;

an estimator that estimates, based on a movement vector of the tracked candidate, a representative vector in the moving image on which the image correction is performed;

an extractor that extracts a candidate in which the movement vector is similar to the estimated representative vector;

a calculator that calculates, based on a drawing position in a frame in which a picture of the extracted candidate is drawn in the moving image and an order of the frame, an arrangement position in which the picture of the extracted candidate needs to be arranged; and a generator that generates a pseudo tomographic image of the living body by drawing the picture of the extracted candidate in the calculated arrangement position.

Further, in the tomographic image processing device according to the present embodiment, it can be configured in such a way that the puncture member is a thin wire acquired by bundling optical fibers, the light-receiving surface is one of stumps of the thin wire, and a direction in which the puncture member punctures the living body is a longitudinal direction of the thin wire.

Further, in the tomographic image processing device according to the present embodiment, it can be configured in such a way that the light-receiving surface is formed in a planar shape having a predetermined angle formed with the longitudinal direction of the thin wire.

Further, in the tomographic image processing device according to the present embodiment, it can be configured in such a way that the corrector performs the image correction by obtaining a coordinate value of each pixel of each frame of the acquired moving image, and performing projecting with the obtained coordinate value as each value of orthogonal coordinates.

Further, in the tomographic image processing device according to the present embodiment, it can be configured in such a way that the light-receiving surface is formed in a conical surface shape in which the longitudinal direction of the thin wire is a central axis direction.

Further, in the tomographic image processing device according to the present embodiment, it can be configured in such a way that the corrector performs the image correction by determining a pole common to each frame of the acquired moving image, obtaining, by a pole coordinate system based on the determined pole, a coordinate value of pole coordinates of each pixel of each frame of the acquired moving image, and performing projecting with the obtained coordinate value of the pole coordinates as each value of orthogonal coordinates.

Further, in the tomographic image processing device according to the present embodiment, it can be configured in such a way that the corrector determines a position of the pole in such a way that a direction of a movement vector of the picture of the extracted candidate and one of axes of the orthogonal coordinates are set closer to a parallel direction.

Further, in the tomographic image processing device according to the present embodiment, it can be configured in such a way that the calculator performs position correction according to a direction of the representative vector in such a way that a distribution of the calculated arrangement position satisfies a predetermined arrangement condition.

Further, in the tomographic image processing device according to the present embodiment, it can be configured in such a way that the calculator performs the position correction by performing expansion and reduction along a direction of the representative vector.

Further, in the tomographic image processing device according to the present embodiment, it can be configured in such a way that the generator draws, in the calculated arrangement position, an average image while the picture of the extracted candidate is tracked.

Further, in the tomographic image processing device according to the present embodiment, it can be configured in such a way that the desired tracking condition is set based on a color of fluorescence emitted from the tissue.

Further, in the tomographic image processing device according to the present embodiment, it can be configured in such a way that the tissue emits fluorescence by giving, to the living body, a fluorescent probe merged with the tissue.

Further, in the tomographic image processing device according to present embodiment, it can be configured in such a way that the tissue emits fluorescence by causing the tissue to generate fluorescent protein.

Further, in the tomographic image processing device according to the present embodiment, it can be configured in such a way that the tissue is a cell or a molecule of the living body, and
the desired tracking condition is set based on whether at least any one of a size, a luminance value, and a shape of a region in which a desired color is drawn falls within a predetermined range.

Further, in the tomographic image processing device according to the present embodiment, it can be configured in such a way that the tracker does not set, as a target of tracking, a picture of tissue that does not satisfy the desired tracking condition.

A tomographic image processing method according to the present embodiment including:

acquiring a moving image in which a cross section of a living body is captured via a light-receiving surface of a puncture member that punctures the living body;

performing image correction of each frame of the acquired moving image, based on a shape of the light-receiving surface;

tracking a candidate for a picture of tissue of the living body that satisfies a desired tracking condition in the moving image on which the image correction is performed;

estimating, based on a movement vector of the tracked candidate, a representative vector in the moving image on which the image correction is performed;

extracting a candidate in which the movement vector is similar to the estimated representative vector;

calculating, based on a drawing position in a frame in which a picture of the extracted candidate is drawn in the moving image and an order of the frame, an arrangement position in which the picture of the extracted candidate needs to be arranged; and generating a pseudo tomographic image of the living body by drawing the picture of the extracted candidate in the calculated arrangement position.

A program according to the present embodiment causing a computer to function as:

an acquirer that acquires a moving image in which a cross section of a living body is captured via a light-receiving surface of a puncture member that punctures the living body;

a corrector that performs image correction of each frame of the acquired moving image, based on a shape of the light-receiving surface;

a tracker that tracks a candidate for a picture of tissue of the living body that satisfies a desired tracking condition in the moving image on which the image correction is performed;

an estimator that estimates, based on a movement vector of the tracked candidate, a representative vector in the moving image on which the image correction is performed;

an extractor that extracts a candidate in which the movement vector is similar to the estimated representative vector;

a calculator that calculates, based on a drawing position in a frame in which a picture of the extracted candidate is drawn in the moving image and an order of the frame, an arrangement position in which the picture of the extracted candidate needs to be arranged; and a generator that generates a pseudo tomographic image of the living body by drawing the picture of the extracted candidate in the calculated arrangement position.

The program can be distributed and sold by being recorded in a non-transitory computer-readable information recording medium. Further, the program can be distributed and sold via a temporary transmission medium such as a computer communication network.

A puncture member according to the present embodiment being a thin wire acquired by bundling optical fibers, wherein the puncture member punctures a living body in a longitudinal direction of the thin wire, and one of stumps of the thin wire is a light-receiving surface for capturing a cross section of the living body.

Further, in the puncture member according to the present embodiment, it can be configured in such a way that the light-receiving surface is formed in a planar shape having a predetermined angle formed with the longitudinal direction of the thin wire.

Further, in the puncture member according to the present embodiment, it can be configured in such a way that the light-receiving surface is formed in a conical surface shape in which the longitudinal direction of the thin wire is a central axis direction.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2021-060196, filed on Mar. 31, 2021, the entire disclosure of which is incorporated by reference herein.

INDUSTRIAL APPLICABILITY

The present disclosure can provide a tomographic image processing device, a tomographic image processing method, a program, and an information recording medium for generating a pseudo tomographic image of a living body from a moving image in which a cross section of the living body is captured via a light-receiving surface of the puncture member that punctures the living body.

REFERENCE SIGNS LIST

101 Tomographic image processing device
111 Acquirer
112 Corrector
113 Tracker
114 Estimator
115 Extractor
116 Calculator
117 Generator
121 Puncture member
122 Light-receiving surface
123 Thin wire
200 Frame
201 Cross section
202 Tissue
203 Movement direction

What is claimed is:

1. A tomographic image processing device comprising:

an acquirer that acquires a moving image in which a cross section of a living body is captured via a light-receiving surface of a puncture member that punctures the living body;

a corrector that performs image correction of each frame of the acquired moving image, based on a shape of the light-receiving surface;

a tracker that tracks a candidate for a picture of tissue of the living body that satisfies a desired tracking condition in the moving image on which the image correction is performed;

an estimator that estimates, based on a movement vector of the tracked candidate, a representative vector in the moving image on which the image correction is performed;

an extractor that extracts a candidate in which the movement vector is similar to the estimated representative vector;

a calculator that calculates, based on a drawing position in a frame in which a picture of the extracted candidate is drawn in the moving image and an order of the frame, an arrangement position in which the picture of the extracted candidate needs to be arranged; and a generator that generates a pseudo tomographic image of the living body by drawing the picture of the extracted candidate in the calculated arrangement position.

2. The tomographic image processing device according to claim 1, wherein the puncture member is a thin wire acquired by bundling optical fibers, the light-receiving surface is one of stumps of the thin wire, and a direction in which the puncture member punctures the living body is a longitudinal direction of the thin wire.

3. The tomographic image processing device according to claim 2, wherein the light-receiving surface is formed in a planar shape having a predetermined angle formed with the longitudinal direction of the thin wire.

4. The tomographic image processing device according to claim 3, wherein the corrector performs the image correction by obtaining a coordinate value of each pixel of each frame of the acquired moving image, and performing projecting with the obtained coordinate value as each value of orthogonal coordinates.

5. The tomographic image processing device according to claim 2, wherein the light-receiving surface is formed in a conical surface shape in which the longitudinal direction of the thin wire is a central axis direction.

6. The tomographic image processing device according to claim 5, wherein the corrector performs the image correction by
determining a pole common to each frame of the acquired moving image,
obtaining, by a pole coordinate system based on the determined pole, a coordinate value of pole coordinates of each pixel of each frame of the acquired moving image, and
performing projecting with the obtained coordinate value of the pole coordinates as each value of orthogonal coordinates.

7. The tomographic image processing device according to claim 6, wherein the corrector determines a position of the pole in such a way that a direction of a movement vector of the picture of the extracted candidate and one of axes of the orthogonal coordinates are set closer to a parallel direction.

8. The tomographic image processing device according to claim 4, wherein the calculator performs position correction according to a direction of the representative vector in such a way that a distribution of the calculated arrangement position satisfies a predetermined arrangement condition.

9. The tomographic image processing device according to claim 8, wherein the calculator performs the position correction by performing expansion and reduction along a direction of the representative vector.

10. The tomographic image processing device according to claim 1, wherein the generator draws, in the calculated arrangement position, an average image while the picture of the extracted candidate is tracked.

11. The tomographic image processing device according to claim 1, wherein the desired tracking condition is set based on a color of fluorescence emitted from the tissue.

12. The tomographic image processing device according to claim 11, wherein the tissue emits fluorescence by giving, to the living body, a fluorescent probe merged with the tissue.

13. The tomographic image processing device according to claim 11, wherein the tissue emits fluorescence by causing the tissue to generate fluorescent protein.

14. The tomographic image processing device according to claim 9, wherein the tissue is a cell or a molecule of the living body, and
the desired tracking condition is set based on whether at least any one of a size, a luminance value, and a shape of a region in which a desired color is drawn falls within a predetermined range.

15. The tomographic image processing device according to claim 14, wherein the tracker does not set, as a target of tracking, a picture of tissue that does not satisfy the desired tracking condition.

16. The tomographic image processing device according to claim 7, wherein the calculator performs position correction according to a direction of the representative vector in such a way that a distribution of the calculated arrangement position satisfies a predetermined arrangement condition.

17. A tomographic image processing method comprising:
acquiring a moving image in which a cross section of a living body is captured via a light-receiving surface of a puncture member that punctures the living body;
performing image correction of each frame of the acquired moving image, based on a shape of the light-receiving surface;
tracking a candidate for a picture of tissue of the living body that satisfies a desired tracking condition in the moving image on which the image correction is performed;
estimating, based on a movement vector of the tracked candidate, a representative vector in the moving image on which the image correction is performed;
extracting a candidate in which the movement vector is similar to the estimated representative vector;
calculating, based on a drawing position in a frame in which a picture of the extracted candidate is drawn in the moving image and an order of the frame, an arrangement position in which the picture of the extracted candidate needs to be arranged; and
generating a pseudo tomographic image of the living body by drawing the picture of the extracted candidate in the calculated arrangement position.

18. A program causing a computer to function as:
an acquirer that acquires a moving image in which a cross section of a living body is captured via a light-receiving surface of a puncture member that punctures the living body;
a corrector that performs image correction of each frame of the acquired moving image, based on a shape of the light-receiving surface;
a tracker that tracks a candidate for a picture of tissue of the living body that satisfies a desired tracking condition in the moving image on which the image correction is performed;
an estimator that estimates, based on a movement vector of the tracked candidate, a representative vector in the moving image on which the image correction is performed;
an extractor that extracts a candidate in which the movement vector is similar to the estimated representative vector;
a calculator that calculates, based on a drawing position in a frame in which a picture of the extracted candidate is drawn in the moving image and an order of the frame, an arrangement position in which the picture of the extracted candidate needs to be arranged; and
a generator that generates a pseudo tomographic image of the living body by drawing the picture of the extracted candidate in the calculated arrangement position.

19. A non-transitory computer-readable information recording medium recording the program according to claim 18.

* * * * *